(12) United States Patent
Banko (10) Patent No.: US 11,039,955 B2
(45) Date of Patent: Jun. 22, 2021

(54) LOW-COST DISPOSABLE ULTRASONIC SURGICAL HANDPIECE

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 393 days.

(21) Appl. No.: 16/001,673

(22) Filed: Jun. 6, 2018

(65) Prior Publication Data

US 2019/0133823 A1 May 9, 2019

Related U.S. Application Data

(63) Continuation-in-part of application No. 15/821,137, filed on Nov. 22, 2017.

(51) Int. Cl.
*A61F 9/007* (2006.01)
*A61B 50/30* (2016.01)
(Continued)

(52) U.S. Cl.
CPC .. *A61F 9/00745* (2013.01); *A61B 17/320068* (2013.01); *A61B 46/10* (2016.02);
(Continued)

(58) Field of Classification Search
CPC ................. A61F 9/00745; A61F 9/007; A61B 17/320068; A61B 17/17;
(Continued)

(56) References Cited

U.S. PATENT DOCUMENTS 3,589,363 A 6/1971 Banko et al.
3,906,954 A 9/1975 Baehr et al.
(Continued)

FOREIGN PATENT DOCUMENTS

CN 106175848 A 6/2016
EP 2521509 B1 1/2011

OTHER PUBLICATIONS

International Preliminary Report on Patentability in corresponding PCT Application No. PCT/US2019/035747, dated Dec. 8, 2020.
(Continued)

*Primary Examiner* — Melanie R Tyson
*Assistant Examiner* — Chima U Igboko
(74) *Attorney, Agent, or Firm* — Leason Ellis LLP (57) ABSTRACT

A disposable ultrasonic handpiece that contains a transducer and a connecting body that tapers to a surgical blade in a single piece. The housing that surrounds the ultrasonic transducer does not require waterproofing for repeated autoclaving. Also, the electrical cord that provides power to the transducer is made of very inexpensive wire, along with a low-cost electrical connector. By making the blade, connecting body with a protective sheet and transducer as a unit with an electrical terminal at the proximal end, they can be plugged and unplugged from a socket and electrical cord in the housing of the handpiece. Thus, only the unit needs to be disposed of after a procedure, making the disposable part of the handpiece even less expensive. The low-cost, disposable handpiece can be packaged along with additional disposable items that are required for one of several types surgeries.

30 Claims, 11 Drawing Sheets (51) Int. Cl.
  *A61B 46/10* (2016.01)
  *A61B 50/33* (2016.01)
  *A61B 17/32* (2006.01)
  *A61B 17/00* (2006.01)
  *A61B 50/15* (2016.01)

(52) U.S. Cl.
  CPC .............. *A61B 50/30* (2016.02); *A61B 50/33* (2016.02); *A61B 2017/0023* (2013.01); *A61B 2017/00411* (2013.01); *A61B 2017/32007* (2017.08); *A61B 2017/320028* (2013.01); *A61B 2017/320069* (2017.08); *A61B 2017/320075* (2017.08); *A61B 2017/320082* (2017.08); *A61B 2017/320084* (2013.01); *A61B 2017/320098* (2017.08); *A61B 2050/155* (2016.02); *A61B 2050/3008* (2016.02)

(58) Field of Classification Search
  CPC ....... A61B 2017/320028; A61B 2017/320075; A61B 2017/320069; A61B 2017/0023; A61B 2017/320082; A61B 2017/32007; A61B 2017/320084; A61B 2017/00411
  See application file for complete search history.

(56) References Cited

U.S. PATENT DOCUMENTS

| | | | |
|---|---|---|---|
| 3,976,077 A | | 8/1976 | Kerfoot, Jr. |
| 3,990,452 A | | 11/1976 | Murry et al. |
| 4,168,447 A | | 9/1979 | Bussiere et al. |
| 4,320,761 A | * | 3/1982 | Haddad .............. A61F 9/00763 408/58 |
| 4,504,264 A | | 3/1985 | Kelman |
| 5,695,510 A | * | 12/1997 | Hood ............. A61B 17/320068 606/169 |
| 6,214,017 B1 | | 4/2001 | Stoddard et al. |
| 6,443,969 B1 | * | 9/2002 | Novak ........... A61B 17/320068 606/169 |
| 7,083,589 B2 | | 8/2006 | Banko et al. |
| 8,348,967 B2 | | 1/2013 | Stulen |
| 8,641,658 B1 | | 2/2014 | Banko |
| 2002/0007200 A1 | | 1/2002 | Desinger |
| 2003/0114873 A1 | | 6/2003 | Banko |
| 2003/0212332 A1 | | 11/2003 | Fenton et al. |
| 2007/0060926 A1 | | 3/2007 | Escaf |
| 2008/0234710 A1 | | 9/2008 | Neurohr et al. |
| 2009/0082716 A1 | | 3/2009 | Akahosi |
| 2014/0029269 A1 | | 1/2014 | Min |
| 2014/0276364 A1 | | 9/2014 | Sussman |
| 2015/0025451 A1 | | 1/2015 | Banko |
| 2016/0106580 A1 | * | 4/2016 | Banko ..................... A61F 9/008 604/22 |
| 2016/0374707 A1 | | 12/2016 | Akagane |
| 2019/0133823 A1 | | 5/2019 | Banko |

OTHER PUBLICATIONS

International Search Report and Written Opinion in corresponding PCT Application No. PCT/US2019/035747, dated Nov. 25, 2019.
U.S. Appl. No. 15/941,366, filed Mar. 30, 2018, Banko.
International Preliminary Report on Patentability in corresponding PCT Application No. PCT/US2018/061940, dated Jun. 4, 2020.
Non-Final Office Action in corresponding U.S. Appl. No. 15/821,137, dated Jun. 24, 2020.
International Search Report and Written Opinion in corresponding PCT Application No. PCT/2018/061940, dated Feb. 26, 2019.
Final Office Action in corresponding U.S. Appl. No. 15/821,137, dated Mar. 30, 2021.

* cited by examiner (PRIOR ART)
Fig. 1

LOW-COST DISPOSABLE ULTRASONIC SURGICAL HANDPIECE

The present invention is a continuation-in-part of U.S. patent application Ser. No. 15/821,137 filed Nov. 22, 2017, the content of which is incorporated herein by reference in its entirety.

TECHNICAL FIELD

The present invention is generally directed to surgical handpieces, particularly disposable ultrasonic surgical handpieces which are conveniently packaged in a disposable tray along with other instruments required for specific types of surgery.

BACKGROUND OF THE INVENTION

The use of ultrasonic surgical instruments for various surgical procedures, including cataract removal, is well known. For example, the phacoemulsification procedure, first disclosed in U.S. Pat. No. 3,589,363 of Anton Banko and Charles D. Kelman, which issued on Jun. 29, 1971, recently reached its 50-year anniversary.

Phacoemulsification handpieces today are essentially the same as the ones developed in the 1970s. They have a very complicated design, are expensive to manufacture, and require sterilization by autoclaving in order to reuse them. The main reason for these disadvantages is the fact that the irrigation and aspiration lines extend through the handpiece and interfere with the performance of the vibrating transducer in the handpiece.

Additionally, the housing that contains the vibrating transducer must be waterproof in order to withstand the high temperatures and pressures of the pressurized steam used during autoclaving. The power cord and the electrical connector must also be able to withstand these high temperatures and pressures of the pressurized steam and must be water proof because they also must be sterilized. This adds considerable expense to the materials and procedures used in the manufacture of the handpiece.

Due to the complexity of the handpieces and the expense of the manufacturing process, ultrasonic phacoemulsification handpieces are generally sold to ophthalmic surgeons with a price ranging from four thousand to seven thousand dollars each. For example, the Alcon® OZil® Torsional Handpiece (Alcon® Model 8065750469) currently retails for $7,492.95 from Medex Supply.

Figure 1:
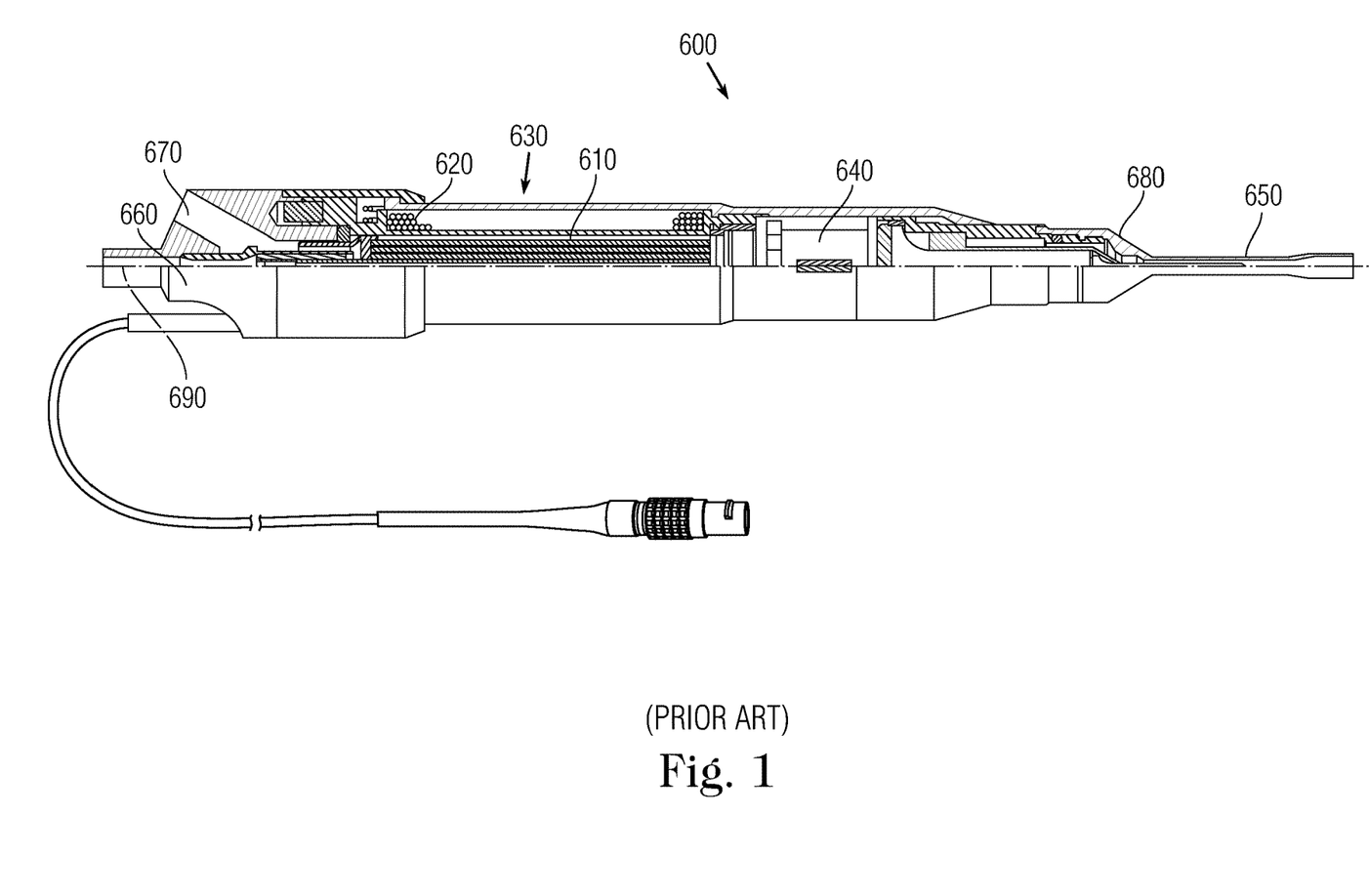
FIG. 1 is a view in partial cross-section of a prior art ultrasonic surgical handpiece.

FIG. 1 shows a prior art handpiece 600 made by Surgical Design Company, the present applicant, with a magnetostrictive ultrasonic transducer 630 that works by expanding and contracting nickel laminations 610 in a magnetic field. The magnetic field is provided by a wire coil 620 that is wound within the handpiece. As the nickel laminations expand and contract, the ultrasonic vibration is amplified and transmitted through a connecting body 640 to the work tip 650 through the connecting body 640. This version of the handpiece contains fluid lines 670, 690 within the vibrating transducer. The center fluid line 690 is the aspiration line that starts with the vibrating hollow phacoemulsification needle work tip 650 and ends at the rear connector 660 of the handpiece. Similarly, the irrigation line 670 enters the rear connector 660 and goes through the nickel laminations 610. From there, the irrigation line enters the irrigation sleeve 680.

FIG. 1 illustrates the complexity of the handpiece 600. This complexity is due to the design of the handpiece, the autoclaving requirements, and the dozens of specialized components that are required to construct the handpiece.

Figure 2:
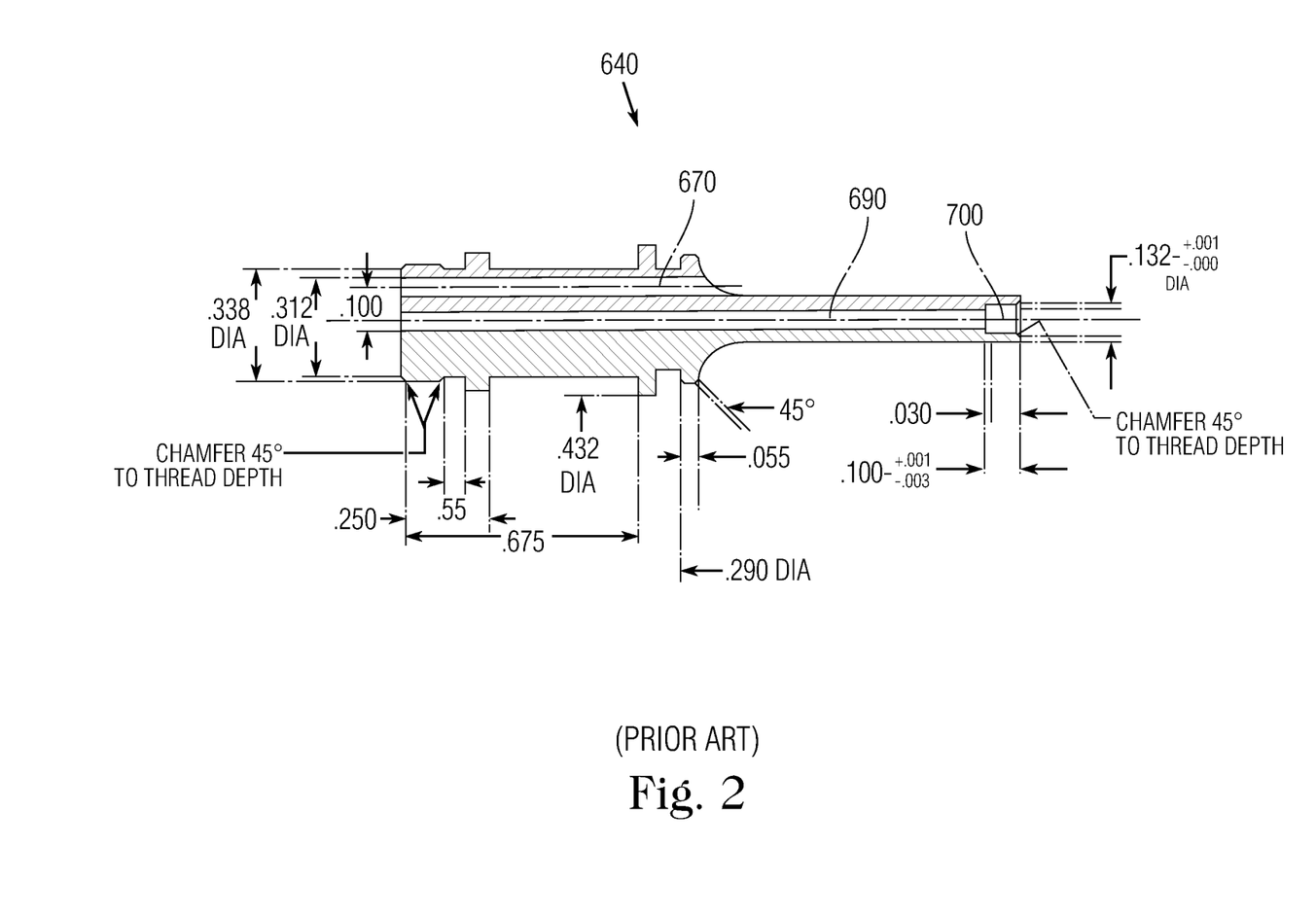
FIG. 2 is a detailed enlarged cross-sectional view with dimensions of a prior art ultrasonic connecting body that is a component of FIG. 1.

FIG. 2 shows an enlarged view of the prior art connecting body 640 for the same handpiece 600. The aspiration line 690, the irrigation line 670, and a thread design 700 where the connecting part 640 attaches to the work tip 650 are shown. FIG. 2 illustrates the complexity and tolerances of the machining required to manufacture a titanium connecting body. This complexity is in part due to the existence of the fluid lines in the body of the handpiece. For example, the tolerances and the radii are specified to thousandths of an inch.

Figure 3:
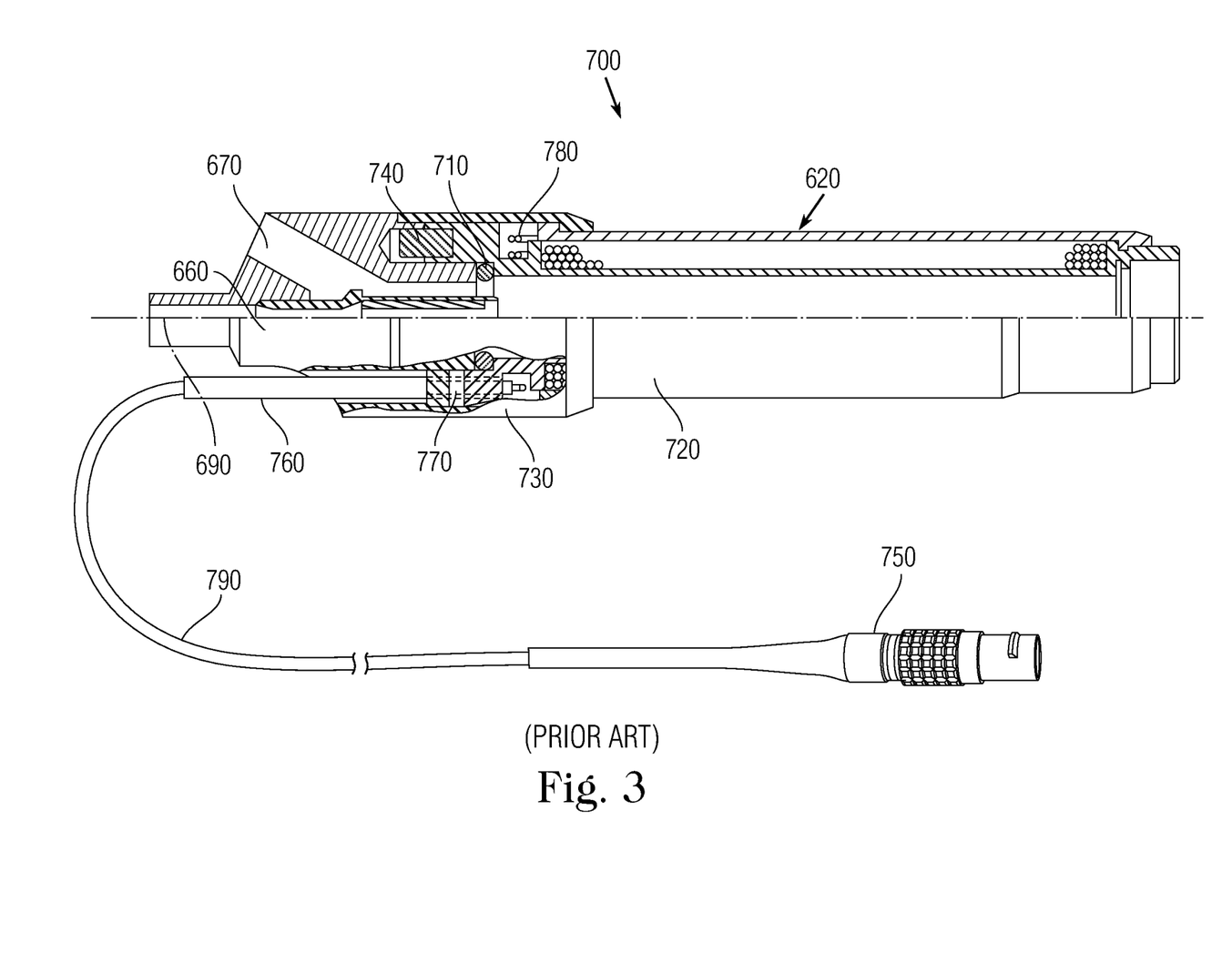
FIG. 3 is a partial cross-section of prior art ultrasonic surgical handpiece that details the coil assembly of FIG. 1.

FIG. 3 shows a typical prior art design for the coil assembly 700 for the same handpiece 600, including the wire coil 620. This portion of the handpiece has center fluid line 690 and irrigation line 670 passing through it. Further, this portion can be seen in relation to the rear fluid connector 660, an O-Ring 710 for confining fluid to the lines, a waterproof housing 720 that surrounds the structure, a coil nut 730 that holds the wire coil 620 in place and a centering pin 740. Also, as shown in FIG. 3 there is a cable connector 750, a power cord 790, a power cord jacket 760, a socket set screw 770 and soldering terminals 780 that allow the ultrasonic signal transmitted over cable 790 to be applied to the coil to create the magnetic field that vibrates the laminations 610, the connecting body and the work tip.

Repeated autoclave cycles require extraordinary efforts to seal the handpiece so that it can withstand the moisture, high pressure, and high temperatures of the autoclaving cycle. For example, in the prior Surgical Design product and other prior products the coil wire 620 is wound onto the handpiece and sealed with an epoxy such as the Huntsman Araldite® CY 8043 Resin Brominated Epoxy. The power cord jacket 760 and the soldering terminals 780 that connect the power cord 790 to the coil wire 620 are sealed with GE RTV133 silicone rubber adhesive sealant that can withstand autoclaving. The power cord 790 is prone to failures from repeated autoclaving because the high pressures and temperatures result in water vapor that gets inside the insulation and corrodes the wires. To minimize corrosion, custom-made power cords need to be used in the handpiece. For example, a nickel-plated wire with a gold coating can be used, which is available from New England Wire Technologies (Lisbon, N.H. 03585). A roll of this custom wire was offered for $28,882.45 per 1000 ft in 2007, but this product is no longer available because of the complexity and cost of manufacturing it.

Because of the expense involved in the manufacture of ultrasonic surgical handpieces, it has so far been impractical to offer them as disposable items. Manufacturers have only offered reusable, autoclavable handpieces.

One of the most common uses for ultrasonic handpieces in the field of ophthalmology is for removing cataracts. Phacoemulsification systems have typically been sold in combination with the console that contains the ultrasonic generator and controls the fluidics. The titanium phacoemulsification tips and external plastic tubing that transports fluid between the surgical system and the handpiece are marketed as disposable, with the rationale that because these components come into contact with the patient's bodily fluids, it is easier and safer to dispose of them after a single use rather than autoclave them. This approach has been very profitable for manufacturers. However, the present inventor has realized that logically this does not make sense since the handpiece itself is being reused after exposure to bodily fluids, even though the channels internal to the handpiece (especially the aspiration tube) are exposed to bodily fluids and are much harder to clean and sterilize.

Concerns about the spread of infection through contaminated body fluids have intensified significantly in recent years with the escalation of HIV/AIDS and other lethal viruses; antibiotic-resistant bacteria; Toxic Anterior Segment Syndrome (TASS); and Prion (Mad Cow) Disease, against which autoclaving may not be 100% effective. For example, with Prion Disease, the proteins are very stable and normal autoclaving may not be enough to denature the structure of the infectious protein and render it harmless. Also, regarding TASS, the Association of periOperative Registered Nurses (Denver, Colo. 80231) reports that > most cases . . . appear to result from inadequate instrument cleaning and sterilization. Other reported TASS cases were associated with glutaraldehyde and detergent residue on instruments, endotoxins from gram-negative bacteria in ultrasonic cleaners, impurities in steam from improperly maintained sterilizers, and degradation of brass surgical instruments sterilized by hydrogen peroxide gas plasma. Prevention of TASS requires thorough cleaning and rinsing of surgical instruments.

("Recommended Practices for Cleaning and Care of Surgical Instruments and Powered Equipment," Association of periOperative Registered Nurses, p. 24) Thorough cleaning does not always occur.

Even when it is effective, the autoclaving process is time-consuming and expensive. The Association of Surgical Technologists (Littleton, Colo. 80120) details 15 practices over 30 pages regarding the complexity of dealing with the decontamination of surgical instruments ("Standards of Practice for the Decontamination of Surgical Instruments," Association of Surgical Technologists, which is incorporated herein by reference in its entirety). These practices involve several different steps and techniques such as placing instruments in a sterile water bath directly after surgery; manually rinsing and flushing the instruments; using ultrasonic cleaning baths with or without enzymatic detergents; etc.

The "Guidelines for the Cleaning and Sterilization of Intraocular Surgical Instruments," compiled by the Ophthalmic Instrument Cleaning and Sterilization (OICS) Task Force (which includes representatives from the American Society of Cataract and Refractive Surgery (ASCRS), the American Academy of Ophthalmology (AAO), and the Outpatient Ophthalmic Surgery Society (OOSS)) gives an overview of the comprehensive training required of nursing and medical staff regarding sterilization procedures. The guidelines, which is incorporated herein by reference in its entirety, recommend that > "Personnel . . . should be properly trained in handling, cleaning, and sterilizing intraocular surgical instruments and subject to periodic oversight. In addition to the general principles of asepsis, this training should also include the cleaning, inspection, preparation, packaging, sterilization, storage, and distribution of intraocular surgical instruments. Appropriate staff should also be trained in related tasks, such as equipment operation and preventive maintenance. They should undergo competency validations by direct observation of performance. Staff education, training, and validation of competency should be updated and documented at least annually and be coincident with the introduction of new surgical equipment, medical devices, or packaging systems."

In addition, each instrument comes with its own specifications for autoclaving from the manufacturer, but it is highly impractical to autoclave instruments individually. All of these procedures require strict quality control guidelines and specifications, as well as careful documentation, and this takes up a significant amount of time.

SUMMARY OF THE INVENTION

In accordance with the invention an ultrasonic surgical handpiece is provided with a solid ultrasonic knife or scalpel located in a sleeve with multiple fluid channels, while retaining a uniform cross section. Further, a cobra cone shape is incorporated into the distal end of the knife to improve it efficiency. The connecting body and the knife or scalpel are manufactured as one piece. Thus, there is no thread between the connecting body and the work tip. This cuts down on manufacturing expense, greatly improves the transmission of ultrasonic vibrational energy from the connecting body to the work tip and is easier to keep clean because there are no threads to provide spaces for bacteria. The increase in efficiency allows for smaller, less expensive parts to be used to achieve the same output energy for removing surgical tissue as a typical, more complex handpiece.

The ultrasonic surgical handpiece contains a housing that is not designed, manufactured, or extensively sealed to be waterproof in order to withstand numerous autoclaving cycles because, being disposable, there is no need to autoclave it. Further, the disposable aspect of the handpiece also allows the power cord and connector to be made of simpler, less expensive materials.

Ultrasonic surgical handpieces have always been complex and expensive to manufacture. For example, phacoemulsification handpieces used for removing cataracts have the irrigation and aspiration fluid lines built into the handpiece. This interferes with the core vibrating transducer within the handpiece, and results in unnecessary complexity. Furthermore, the autoclaving of these handpieces and materials management is a huge disadvantage to the operating room staff. This complexity and its cost are avoided with the present invention wherein the fluid lines do not pass through the handpiece and it can be made to be disposable.

The benefits of having an entirely disposable ultrasonic surgical handpiece are numerous. As the European Pharmaceutical Review (Kent, TN16 1NU, UK) explains in general: "The advantages of single-use technology can be summarized as: eliminating the need for cleaning; removing requirements for in-house sterilization (typically by autoclaving) for all components; reducing the use of cleaning chemicals; cutting storage requirements; lowering process downtime; and increasing process flexibility and reducing cross-contamination risks." (Dr. Tim Sandle, "Strategy for the adoption of single-use technology," 22 Mar. 2018, which is incorporated herein by reference in its entirety.)

A disposable phacoemulsification handpiece that is included in a disposable tray that contains all the equipment required for a surgeon to do a cataract procedure is an additional approach to the present invention with further benefits.

Further, typically the work tip is vibrated axially. However, it is known that the work tip can be made more efficient during phacoemulsification if the work tip additionally vibrates side-to-side. See for example the transverse vibration of the J. Shock Phaco Fragmentation Unit and the OZil® Torsional Handpiece, both made by Alcon®, in which a component of motion perpendicular to the axis is present in addition to longitudinal vibration due to eccentric masses in the vibrator in general and in the tip in particular.

This is beneficial regardless of the type of work tip, i.e., blade, tube or rod. According to the present invention, simpler ways to establish the side-to-side vibration are provided. For example, a stationary or slidable pin can be located in an angled slot in the center of the blade to create the side-to-side movement as the work tip vibrates axially. This side-to-side movement will be at the axial frequency if the pin is stationary or a higher frequency based on the rate of movement of the pin. In a second embodiment, a pin with a driving force perpendicular to the axial direction of the rod can apply a periodic variable pressure to the rod at the rate of the driving force and independent of the axial frequency. A still further embodiment can have a stationary pin which engages an angled or curved portion of the rod or blade so that as it vibrated the portion rides along the pin and is bent out of the axial direction at the axial direction frequency.

BRIEF DESCRIPTION OF THE DRAWINGS

The foregoing and other objects and advantages of the present invention will become more apparent when considered in connection with the following detailed description and appended drawings in which like designations denote like elements in the various views, and wherein.

DETAILED DESCRIPTION OF THE INVENTION

Figure 4A:
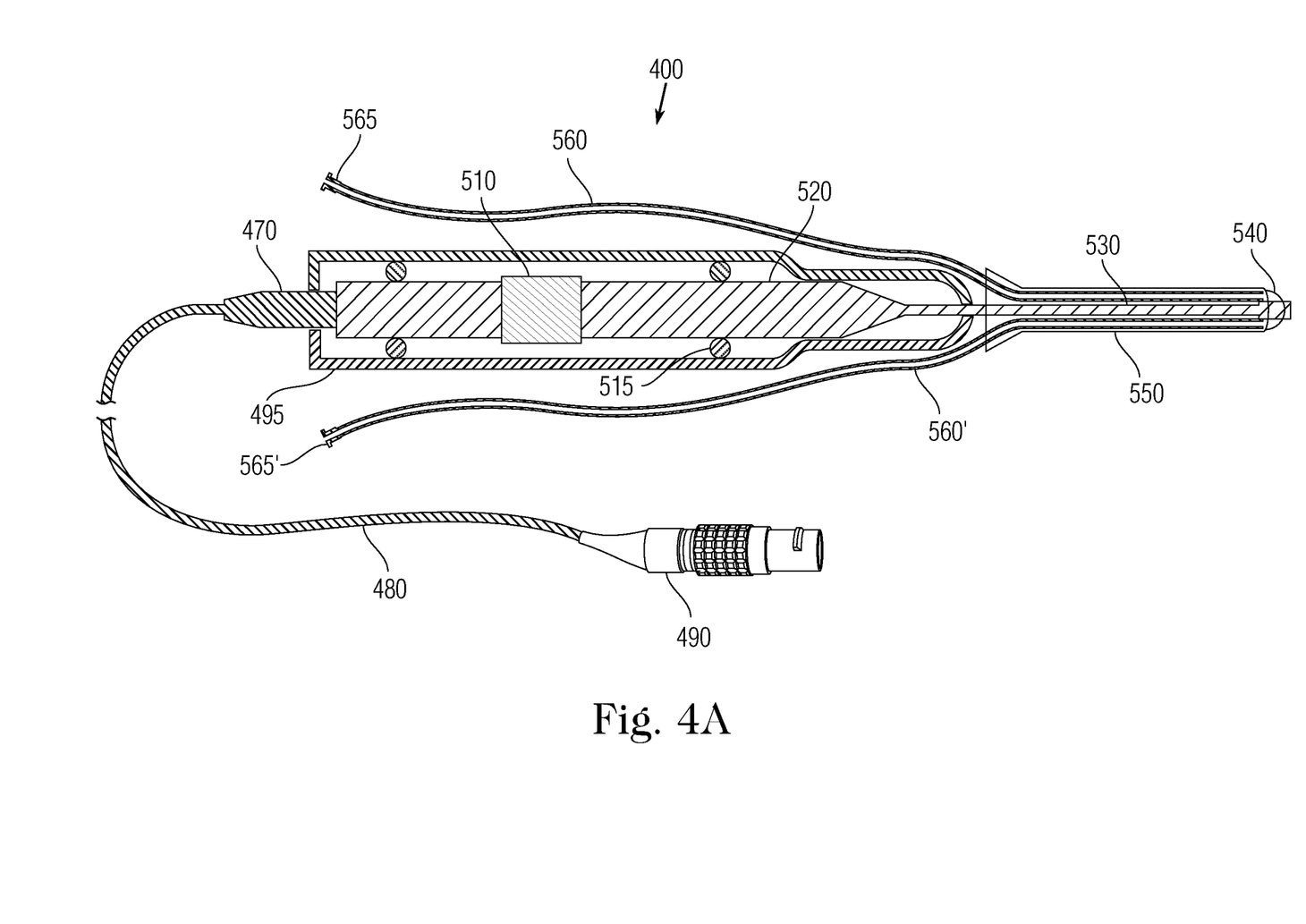
FIG. 4A is a cross-section of a completely disposable ultrasonic surgical handpiece with a single-piece connecting body and work tip, external irrigation and aspiration fluid tubes and a piezoelectric crystal transducer.

FIG. 4A shows a disposable ultrasonic surgical handpiece 400 according to the present invention. This handpiece is unique in its design simplicity. The housing 495 can be made of plastic or metal, but does not require waterproofing to withstand the moisture, high temperatures, and high pressures of autoclaving. The internal elements can be fixed to the housing 495 with simple plastic or elastic components 515, e.g., O-rings. No epoxies or sealants are required between the housing 495 and the internal components. The power cord connector 470 also does not require epoxies or silicones to keep moisture from entering the rear of the handpiece. In addition, the power cord 480 can be made of simple, inexpensive electrically conducting wires covered with insulation, where the insulation is only required for the purpose of isolating the electrical conductivity of the wires. It is not necessary to insulate the wires against corrosion due to moisture, high temperatures, and detergents or other chemicals that are encountered during autoclaving.

The ultrasonic transducer 510 of this handpiece 400 can be either magnetostrictive or made of ceramic piezo crystals. The connecting body 520 extends from the transducer 510 into a long flat blade 530 with a chisel work tip 540. This configuration has been described in a previous patent application, i.e., Surgical Design Corp patent application Ser. No. 15/821,137 filed Nov. 22, 2017, to which priority is claimed and which is incorporated herein by reference in its entirety. Having the connecting body and the work tip as a single piece has several significant advantages. Manufacturing a single-piece connecting body costs only a fraction of the cost of manufacturing a connecting body and work tip in two pieces with threads that screw them together. For example, creating the thread 700 in FIG. 2 requires precision machining with extremely tight tolerances (thousandths of an inch). In addition to the expense, unless the thread on the work tip exactly matches the thread on the connecting body, there is a loss of energy. In particular, there is never one-hundred percent efficiency in coupling the two parts, so there is a power loss especially during ultrasonic vibration when the connecting body transmits the vibration at a frequency of anywhere from 44 kHz/s to 50 kHz/s. An arrangement in which the connecting body and work tip are a single piece is thus much more efficient for transmitting ultrasonic vibration and offers cost-savings that are so significant that the handpiece can be disposable.

Figure 5A:
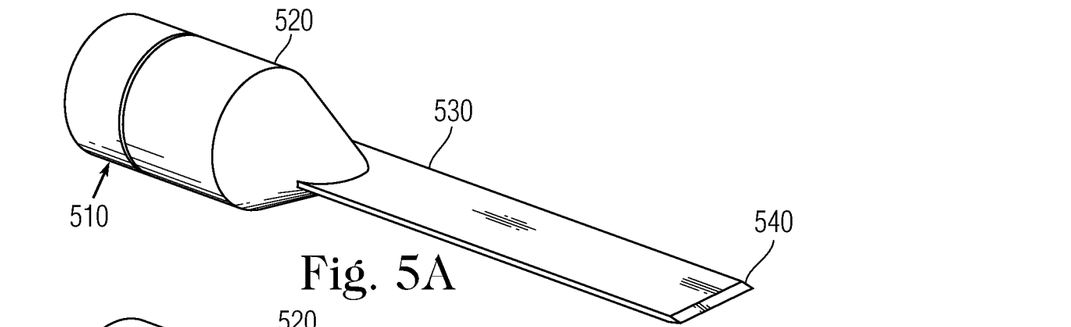
FIGS. 5A-5D show various work tip configurations for use with the present invention.
Figures 5B, 5C, 5D:
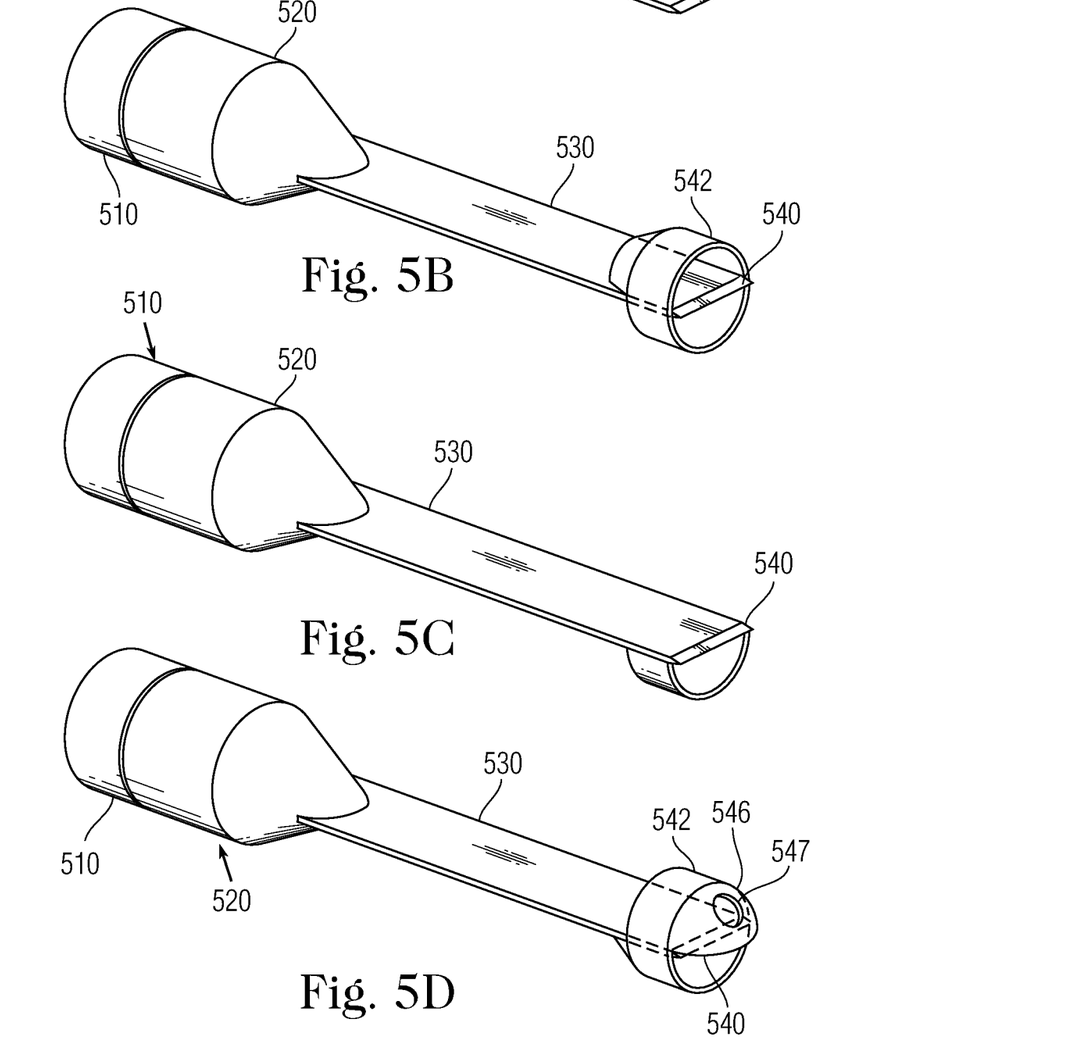

The distal work tip 540 can have several configurations, as described in a previous Surgical Design Corp. patent application Ser. No. 15/941,366 filed Mar. 30, 2018, which is incorporated herein by reference in its entirety. However, for the purposes of this invention, these work tips are now part of an ultrasonic surgical instrument that does not require that the housing, power cord, or electrical connector be waterproof. The various work tip configurations as shown in FIG. 5A-5D are as follows:

a single-piece connecting body 520 that tapers to a blade 530 and then to a sharp chisel shape forming a work tip 540 at its distal end (FIG. 5A);

a single-piece connecting body 520 wherein the distal end of the work tip has a narrow tube 542 attached to it and terminates in a sharp chisel-shaped work tip 540 (FIG. 5B);

a single-piece connecting body 520 wherein the distal end of the work tip has half of a narrow tube 544 attached to it and terminates in a sharp chisel shaped work tip 540 (FIG. 5C); and a single-piece connecting body 520 wherein the distal end of the work tip has a narrow tube 542 attached to it, with a quarter of a sphere shape 546 with a small hole 547 in it attached to the upper portion of the tube 542 (FIG. 5D).

Power is provided to the handpiece from a connector 490 that is attached to a console (now shown) that contains an ultrasonic signal generator and also controls the fluidics. The ultrasonic signal is passed from connector 490 through cable 480 to plug 470 on the proximal end of the workpiece 400. The power cord parts 470, 480 and 490 differ from similar parts 750 and 790 of the prior art as shown in FIG. 3, in that they are disposable, so the never have to withstand autoclaving. As a result, they need not be waterproof or corrosion resistant, and as a result can be less expensive than the prior art.

During a typical phacoemulsification procedure an incision is made in the eye, and the surgeon extends the work tip 540 through the incision and into the vicinity of a cataract that is to be removed. The console is then operated so that fluid is directed into the incision and also withdrawn from the incision. For example, irrigation fluid from the console may be passed through flexible plastic tube 560 attached to the console by connector 565. Fluid may be aspirated from the incision through tube 560' and delivered back to the console or a separate disposable container (not shown) through connector 565'. Tube 560' may extend to a rotary peristaltic pump on the exterior of the console, but not into the console itself. It should be noted that the fluid lines and the blade 530 are surrounded by a sheath 550 at the distal end of the handpiece that keeps these elements together as they pass into the incision. When the cataract is contacted with the work tip 540, the console provides ultrasonic electrical signals through cable 480 to the transducer 510, which causes the tip to vibrate at an ultrasonic frequency and to chop or emulsify the cataract. During this procedure the surgical site is bathed in irrigation fluid and the pieces of cataract are withdrawn with the aspiration fluid. In this operation bodily fluid is entrained with the aspiration fluid. Also, it is possible for bodily fluid to pass through sheath 550 along the knife 530 and the exteriors of the tubes 560, 560'. However, this fluid cannot pass along the handpiece because of the front section of the housing 495 of the handpiece, which may be augmented with a seal or O-ring (not shown).

After phacoemulsification a cleanup procedure may be used to remove epithelial cells while preventing the tearing of the capsular bag of the eye. This can be done with a separate irrigation/aspiration (I/A) tool. As an alternative there are dual mode handpieces that can be converted from use in phacoemulsification to cleanup. Such a handpiece is disclosed in U.S. patent application Ser. No. 15/941,366 filed Mar. 30, 2018, which has been incorporated herein by reference. When the phacoemulsification procedure or the phacoemulsification and cleanup procedures when accomplished with a single tool are over, the entire handpiece with its connected fluid tubes and electrical power lines can be disposed of. If the aspiration line 560' is directed to a waste container through connector 565', that container would also be discarded. Thus, there is nothing to sterilize before operating on the next patient. Instead a new handpiece with its connected fluid tubes and electrical power lines is connected to the console and the next procedure begun. The savings in time between procedures allows for more procedure to be performed in a single session, which can lower the overall cost of each procedure. The elimination of the need for autoclaving also provides an additional saving in time and expense that can lead to a further reduction in cost.

Figure 4B:
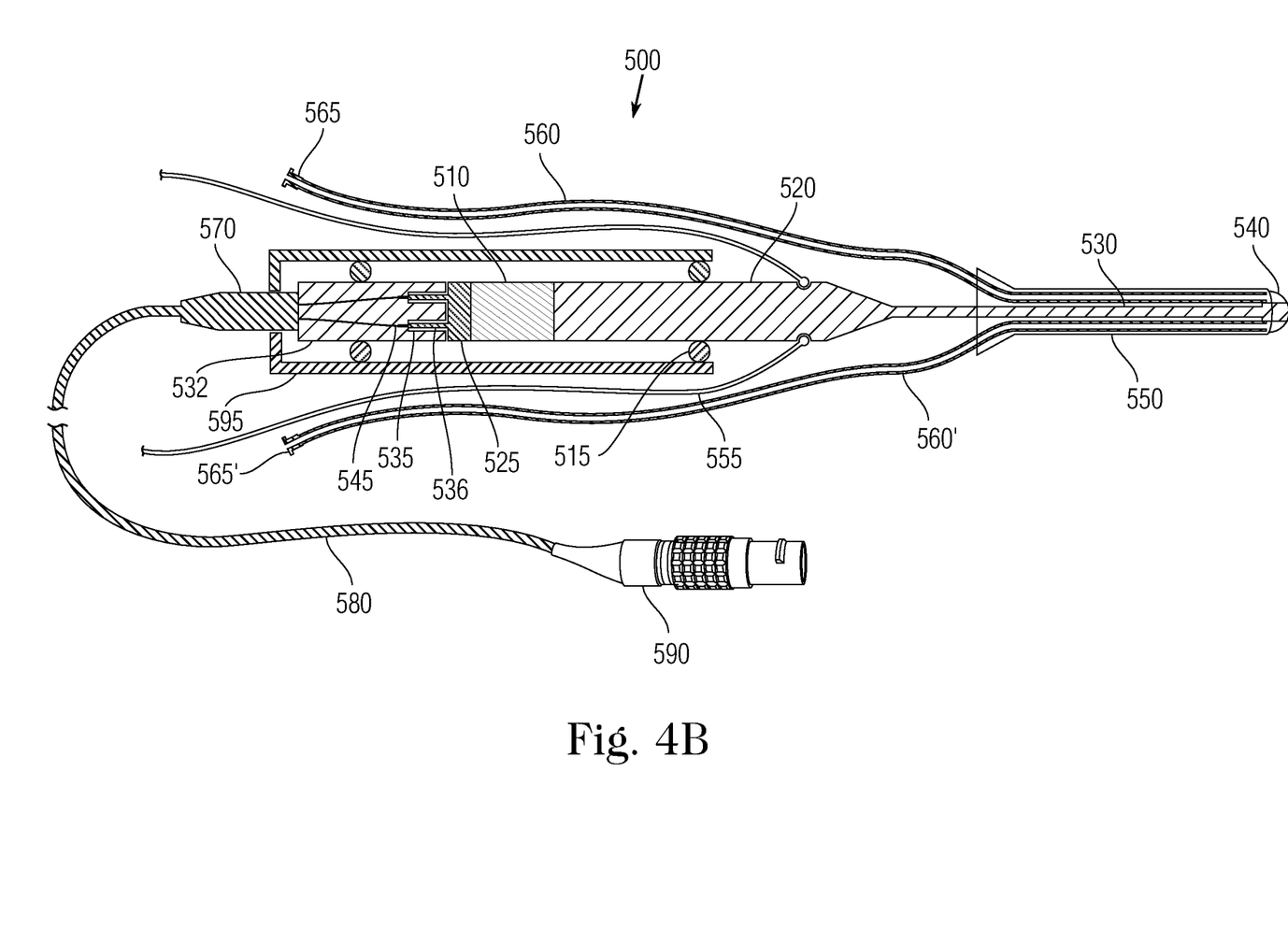
FIG. 4B is a cross-section of a partially disposable ultrasonic surgical handpiece with a single-piece connecting body and work tip, external irrigation and aspiration fluid tubes, and a piezoelectric crystal transducer that electrically plugs into an ultrasonic signal socket in a housing so that the transducer, connecting body with a protective sheet and work tip only are disposed after a single use.
Figure 4C:
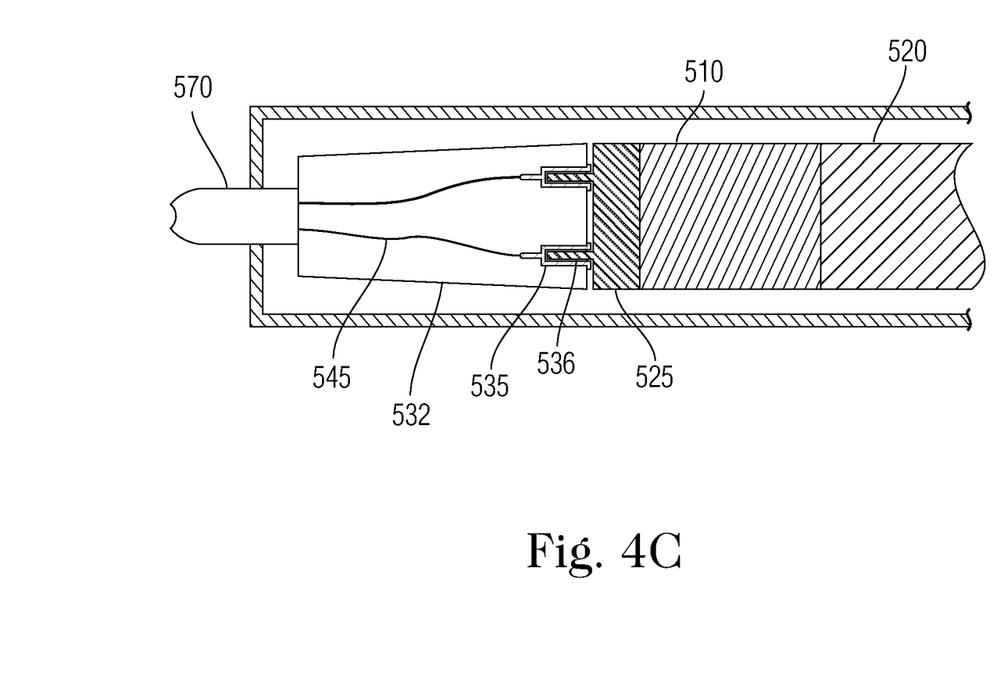
FIG. 4C is an enlarged detailed view of the electrical socket at the distal end of the connecting body of the handpiece of FIG. 4B.

FIG. 4B discloses a handpiece 500 which is similar to handpiece 400 of FIG. 4A. However, instead of the ultrasonic signals being hard wired from plug 470 to piezo crystals 510, a plug 570 passes the signals through a socket 532 to a plug 525 on the proximal end of the crystals 510. The socket 532 provides wires 545 that are connected to sockets receptacles 535. See FIG. 4C. The transducer 510 has a plug or terminal 525 at its proximal end. The terminal has pins 536 that are designed to be removably inserted into receptacles 535 of socket 532 in order to provide ultrasonic electrical power to crystal transducer 510. The terminal 525 and the socket 532 can be reversed so that the socket is on the transducer and the terminal is on the cable plug 570. The pins and receptacles can be generically referred to as "connectors."

Handpiece 500 also differs from handpiece 400 in that the distal end of the housing 595 is generally open to allow the connecting body 520 to pass through. However, that opening is sealed with an O-ring 515. Further, the design includes a surgical drape or sterile sheet 555 that is fastened to the distal end of the connecting body and can be draped over the handpiece housing. As a result, the sheet 555 protects housing and the power cable from bodily fluids. With the design of FIG. 4B, the knife 530, connecting body 520, transducer 510 and terminal 525 may be detached as a unit from socket 532, so that the socket 532, plug 570, cord 580 and connector 590 need not be discarded and because of surgical sheet 555, they also do not need to be sterilized between procedures on different patients. In effect the connecting body with the sheet 555 is pulled in the distal direction out of the opening in the housing so that it, the transducer 510 and terminal 525 slide out of the housing 595 beyond the O-ring 515. By saving the housing 595, socket 532 and powerline, and avoiding the need to sterilize them between procedures, the cost of the disposable parts is greatly reduced, making this a much more viable option.

Figure 4D:
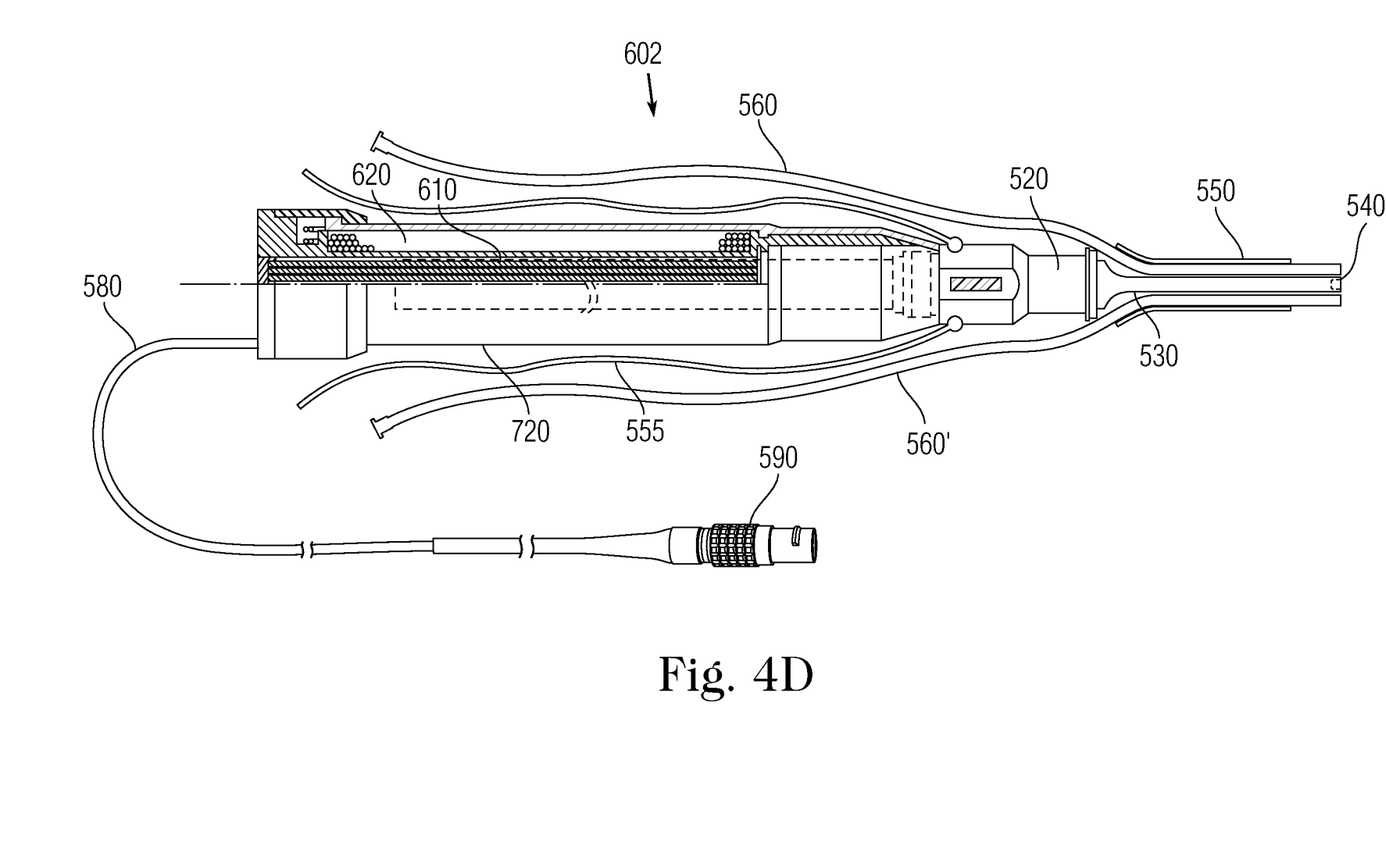
FIG. 4D is a cross-section of a completely or partially disposable ultrasonic surgical handpiece with a single-piece connecting body and work tip, external irrigation and aspiration fluid tubes, and a magnetostrictive transducer with laminations connected to the connecting body that slide with in an electrical coil in a housing so that the laminations, connecting body with a protective sheet and work tip only are disposed after a single use.

FIG. 4D is a design for a handpiece 602 that is similar to handpiece 500 of FIG. 4B, but for use with a magnetostrictive transducer such as that shown in handpiece 600 of FIG. 1 instead of a piezoelectric crystal transducer. In fact, because piezoelectric crystals need direct connection to an electrical supply, while the nickel laminations 610 of a magnetostrictive transducer only need electromagnetic connection to the coils 620 of the handpiece, the connecting body 520 is easily separated from the rest of the handpiece without any special plug/socket arrangement, presenting a further reduction in cost.

As shown in FIG. 4D, the handpiece and power cord could be disposed of because the tubes 560, 560' do not run through the handpiece. However, by including a sheet 555 attached to the connecting body 520 as shown in FIG. 4D, the rest of the handpiece and the power cord are protected from bodily fluids. This includes any fluids that may travel along the blade to the distal end of the connecting body. With this arrangement, when the surgical procedures are completed, all that is necessary is to pull the connecting body 520 so that it and the laminations 610 are withdrawn from the portion of the housing 720 with the surrounding coils 620. The blade 530, connecting body 520, tubing 560,560' and sterile sheet 555 are then discarded. However, the handpiece, including the coils 620, and the power cord 580, 590 can be retained and reused without the need for sterilization.

Figure 6A:
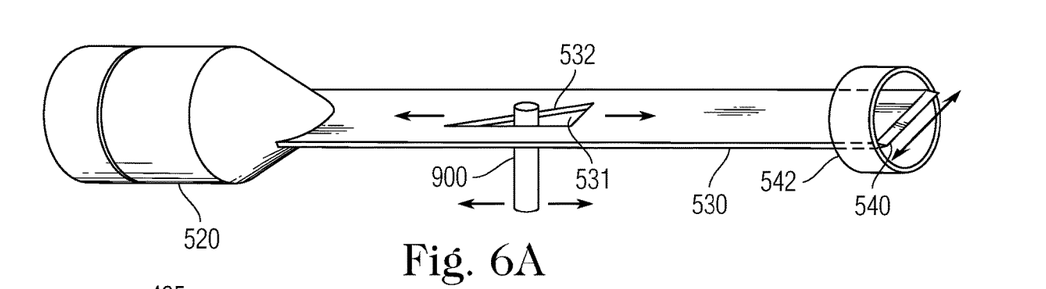
FIGS. 6A-6D show various structures for imparting a side-to-side vibration to the work tip along with its axial vibration.

Typically, the work tip 540 is vibrated axially. However, it is known that the work tip can be made more efficient during phacoemulsification if the work tip additionally vibrates side-to-side. This is beneficial regardless of the type of work tip, i.e., blade, tube or rod. According to the present invention, simpler ways to establish the side-to-side vibration are provided. For example, FIG. 6A shows a pin 900 located in an angled slot 531 in the center of the blade 530.

The pin may be stationary or movable in the axial direction. When the pin is stationary axial forward movement (to the right in FIG. 6A) of the blade causes the pin to contact the angled edge 532 of the slot, which forces the blade more and more to one side. During the rearward movement of the blade returns to its center position. The pin 900 can be fastened either to the housing 495 as shown in FIG. 4A or to the expanded proximal end of the sheath 550, which may be made of a hard-plastic material or metal. As a result, the blade (rod or tube) will vibrate side-to-side at the same frequency as the axial motion. However, if the pin moves axially, the side-to-side frequency can be increased based on that movement, but it will be related to the axial movement of the blade.

The contact between the edge 532 and the pin 900 may create friction that generates some heat in the blade and wear on the pin. One way to reduce this is to make the pin of a low friction materials, e.g., Teflon®. Further, if the blade and pin are disposable after each use, they will be discarded before they loses their effectiveness. Movement of the pin 900 may be by means of a small transducer on the housing 495 or the sheath 550 that is provided with an electrical signal, e.g., from the console.

If the connecting body is designed to be disposable, the housing arrangement of FIG. 4B is required. In such a case, the pin should be mounted on the expanded distal end of the sheath 550 or their will need to be an extension of the housing 595 to the vicinity of the blade 530.

Figure 6B:
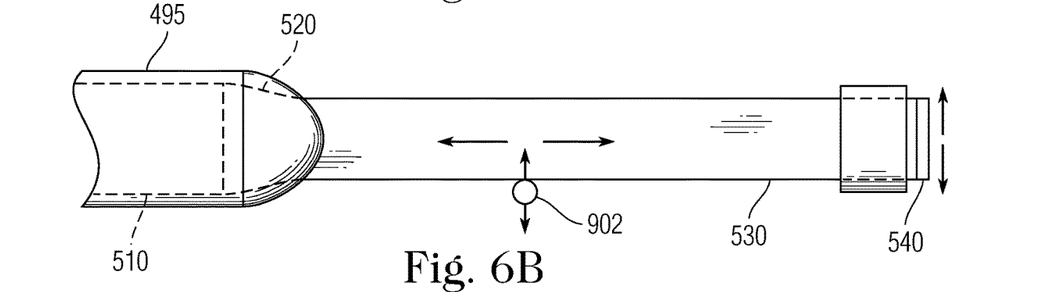

In a second embodiment in FIG. 6B, there is a pin 902 moved by a driving force perpendicular to the axial direction of the rod. It applies a periodic variable pressure to one side of the rod to create the side-to-side motion. The driving force can come from a transducer (not shown but indicated by arrows at the pin) located in the wall of the housing 495 or the sheath 550. The transducer may have a self-generator or be supplied with a variable electrical signal from the console. The main transducer 510 causes axial movement of the blade 530, while the transducer attached to pin 902 causes perpendicular movement of the pin and hence the blade. The arrangement of FIG. 6B has a benefit over the embodiment of FIG. 6A in that the side-to-side motion can be at a different and independent frequency from that of the longitudinal vibration. However, this benefit comes at the expense of additional elements in the design. In order to reduce friction, the pin 902 may be made of a material such as Teflon.

Figure 6C:
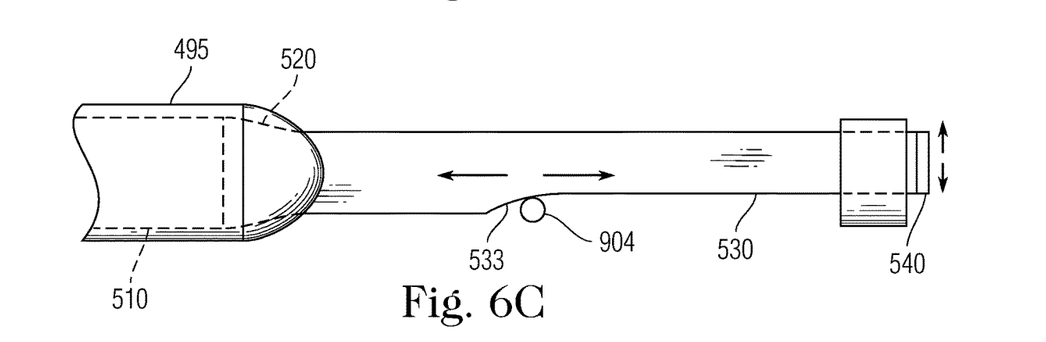

A still further embodiment is shown in FIG. 6C. In that design a curved area 533 is created in the rod or blade 530 on one side. A stationary pin 904 extending from the housing or sheath engages the area 533 so that it bents the blade out of the axial direction creating side-to-side movement at the same frequency as the axial movement.

Figure 6D:
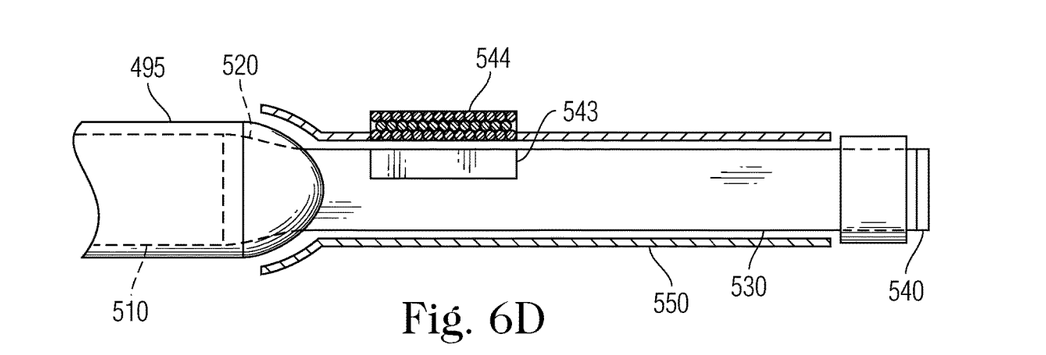

FIG. 6D shows another embodiment in which the side-to-side vibration is caused by a magnetic field. In particular, a magnetic coil 544 is set up on the housing or sheath 550. It is fed with an electrical signal from the console or otherwise. A magnet 543 is placed on the blade 530. When an alternating magnetic field is set up by the coil, it causes the blade to vibrate from side-to-side.

A disposable phacoemulsification handpiece that is included in a disposable tray that contains all the equipment required for a surgeon to do a cataract procedure is an ideal way of addressing the problems that traditional handpieces raise.

Figure 7:
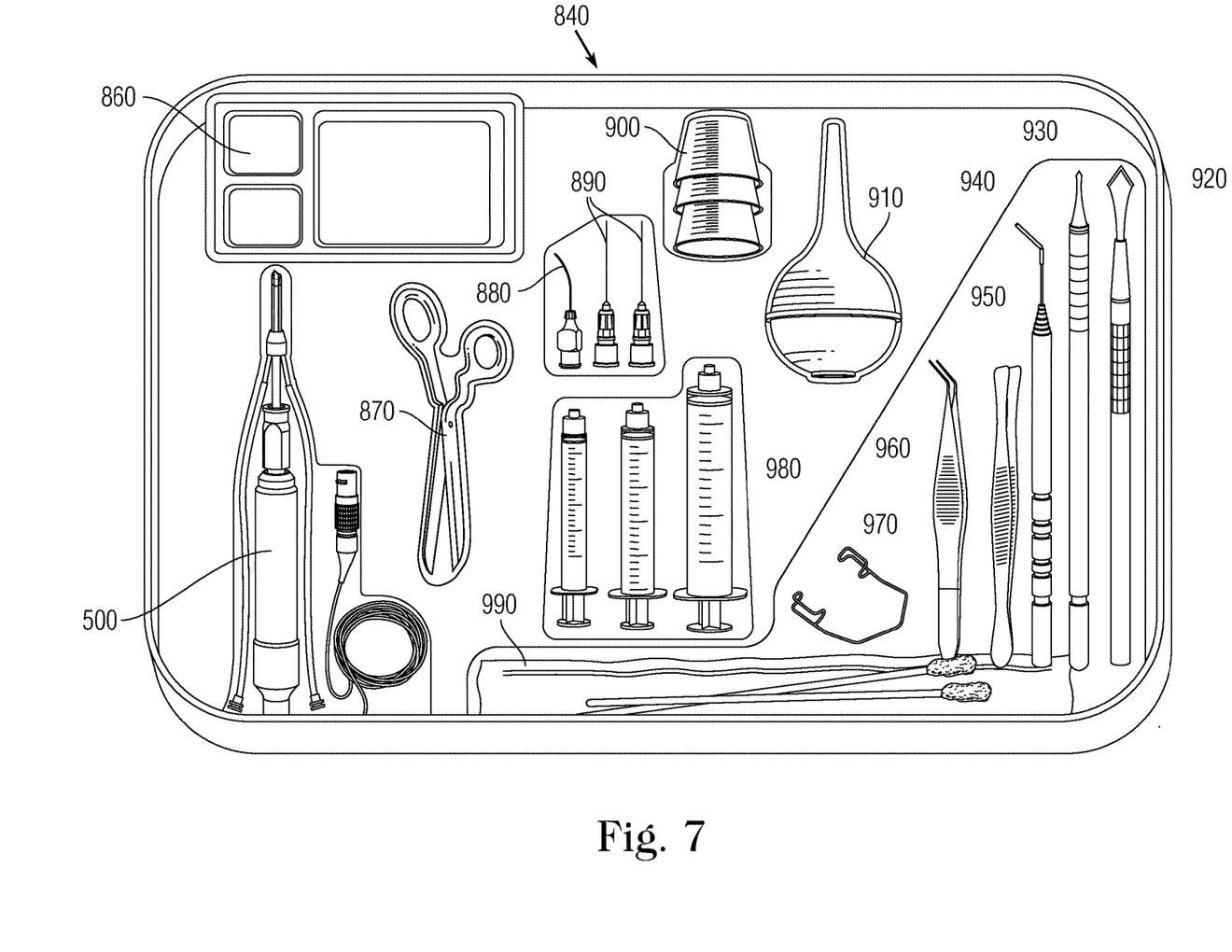
FIG. 7 is a disposable sterile surgical pack with an ultrasonic surgical handpiece.

FIG. 7 illustrates the components of a disposable surgical tray 840 that includes a handpiece 500 described in this invention. The tray contains the following items:

(a) Ultrasonic surgical handpiece 500 with attached fluid tubes and electrical cord
(b) Prep tray 860
(c) Scissors 870
(d) Hydrodissection cannula 880
(e) 2 30-gauge Cannula 890
(f) Medicine cups 900
(g) Ear/ulcer syringe 910
(h) Keratome blade 920
(i) Paracentesis blade 930
(j) Lens hook 940
(k) Forceps 950
(l) Capsulorhexis forceps 960
(m) Eye speculum 970
(n) 2-4 Syringes 980 of various sizes
(o) Sterile cotton tipped applicators 990

Figure 8:
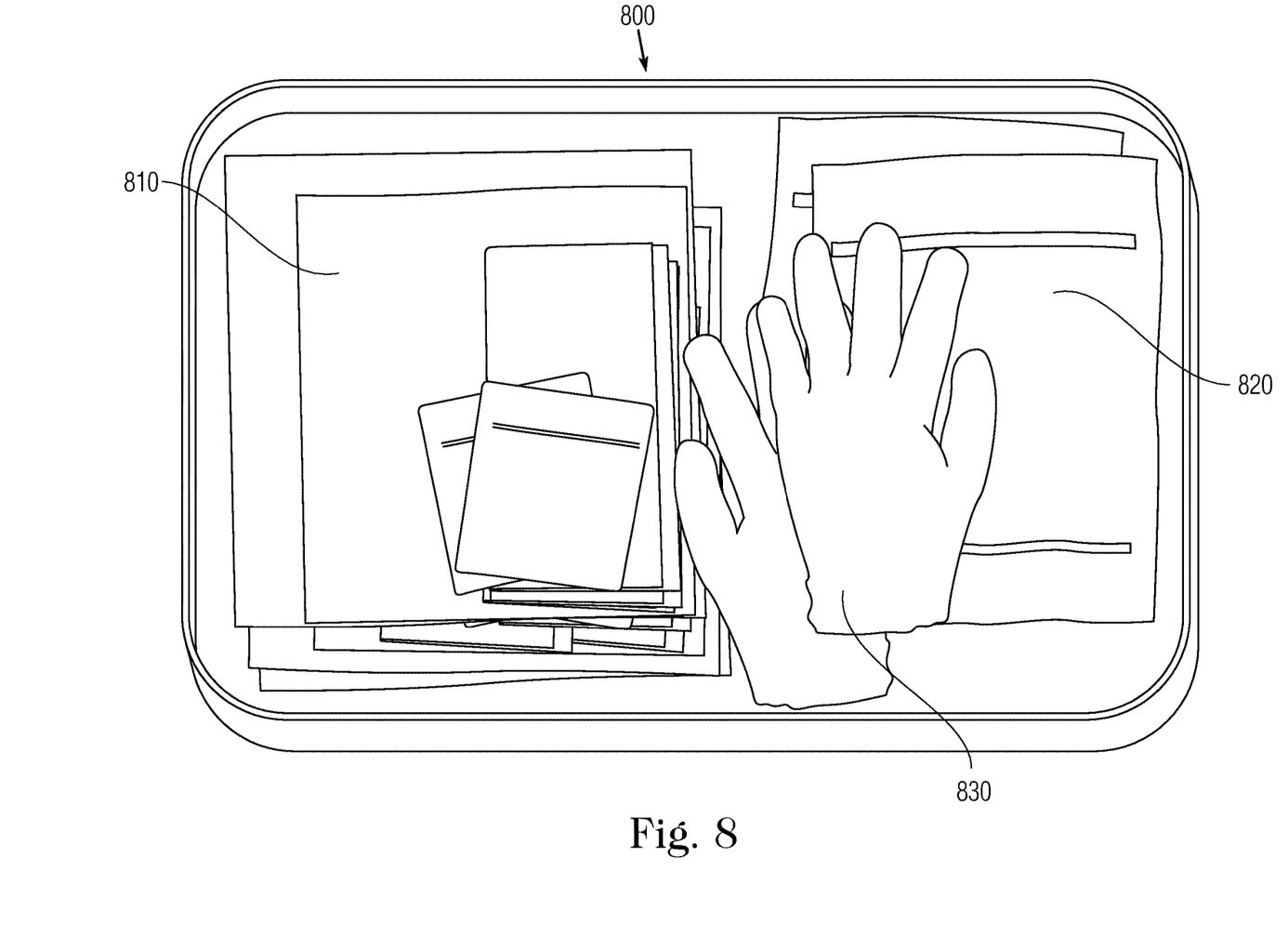
FIG. 8 is a disposable sterile surgical pack with a surgical drape; an ophthalmic drape; a mayo stand cover; a table cover; twenty gauze pads; two large surgical gowns, and gloves.

FIG. 8 illustrates the components of a second disposable surgical tray that does not include the surgical instruments. The tray contains the following:

(a) 1 surgical drape, 1 ophthalmic drape, 1 mayo stand cover, 1 table cover, 20 gauze pads 810
(b) 2 large surgical gowns 820
(c) Gloves 830

With the cost savings from (a) eliminating the threaded connection between the connecting body and blade, and perhaps between the blade and work tip; (b) eliminating the need to form fluid channels through the handpiece; and (c) eliminating the hollow tube work tip and replacing it with a blade, the cost of the hand piece can be sufficiently low that it can be a disposable single-use item. Making the handpiece disposable means there is no longer a need to sterilize the handpiece after use. The sterilization process typically involves moisture and high temperatures. As a result, the handpiece, particularly the ultrasonic transducer, must be made to withstand sterilization, e.g., making the coils of gold wire. Thus, by avoiding sterilization the transducer can be made of less extensive parts (e.g., copper wire) making it even more feasible to have it as a single-use disposable item.

Even more savings can be realized by making the work tip, blade, connecting body, transducer and at least part of an electrical terminal such that they can be plugged and unplugged from a socket, housing and electrical cord of the handpiece. Thus, only the former need to be disposed of and the later can be reused without sterilization because of a sheet 555 attached to the connecting body and draped over the housing during a phacoemulsification procedure. With a magnetoelectric transducer, there is no need for a plug/socket arrangement since the nickel laminations can simply be slid out of the coils in the hand piece.

While the invention has been shown and described in connection with the removal of a cataract from the eye of a patient and subsequent I/A clean up, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. An ultrasonic surgical handpiece comprising:
a transducer;

a single-piece connecting body that tapers to a blade and then to a sharp chisel shape to form a work tip at its distal end, said transducer attached to said connecting body;
a housing for containing at least part of the connecting body and the transducer, said housing being formed without provisions for water proofing;
irrigation and aspiration fluid lines that extend along the blade to the chisel shape, and extend around the housing; and
a power cord for providing an ultrasonic signal to said transducer, said power cord being attached to said housing and being formed without provisions for water proofing or corrosion resistance.

2. The ultrasonic surgical handpiece according to claim 1 wherein the distal end of the work tip has a narrow tube attached to it and terminates in the sharp chisel shape.

3. The ultrasonic surgical handpiece according to claim 1 wherein the distal end of the work tip has half of a narrow tube attached to it and terminates in the sharp chisel shape.

4. The ultrasonic surgical handpiece according to claim 1 wherein the distal end of the work tip has a narrow tube attached to it, said tube having a quarter of a sphere shape with a small hole attached to the upper portion thereof.

5. The ultrasonic surgical handpiece according to claim 1 wherein the transducer is a magnetostrictive ultrasonic transducer.

6. The ultrasonic surgical handpiece according to claim 5 further including a sheet secured about the connecting body and being designed so it can be draped over the housing, wherein laminations the connecting body are retained on the connecting body coils of the transducer and retained in the housing such that the connecting body with the laminations can be withdrawn from the housing and the coils and disposed after a single use along with the fluid lines, and the housing, coils, and power cord can be retained and reused without sterilization.

7. The ultrasonic surgical handpiece according to claim 1 wherein the transducer is a ceramic crystal transducer.

8. The ultrasonic surgical handpiece according to claim 7 further comprising:
a terminal with connectors, said terminal being located at a proximal end of the ceramic crystal transducer and connectors of the terminal being electrically attached to crystals of the ceramic crystal transducer;
a socket with connectors, said socket being attached to a proximal end of the housing, the connectors of the socket being electrically connected to the power cord and the connectors of the terminal being plugged into or unplugged from the connectors of the socket; and
wherein a distal end of the housing has an opening through which the connecting body, transducer and terminal may be removed as the terminal is unplugged from the socket.

9. The ultrasonic surgical handpiece according to claim 8 further including a surgical sheet secured about the connecting body and being designed so it can be draped over the housing.

10. The ultrasonic surgical handpiece according to claim 8 further including a seal at the distal opening in the housing to secure the interior of the housing when the connecting body is in place and pins of the terminal are plugged into receptacles of the socket.

11. A disposable surgical sterile pack comprising the materials according to claim 10 and at least one of:
a surgical drape;
an ophthalmic drape;
a mayo stand cover;
a table cover;
twenty gauze pads;
two surgical gowns, large; and
gloves.

12. The ultrasonic surgical handpiece according to claim 8 wherein the connectors of the terminal are pins and the connectors of the socket are receptacles.

13. A disposable surgical sterile pack comprising the materials according to claim 12 and at least one of:
a surgical drape;
an ophthalmic drape;
a mayo stand cover;
a table cover;
twenty gauze pads;
two surgical gowns, large; and
gloves.

14. A disposable sterile surgical pack comprising the ultrasonic surgical handpiece according to claim 6 and at least one of:
a prep tray;
a pair of scissors;
an ear/ulcer syringe;
an eye speculum;
two to four syringes of various sizes;
a hydrodissection cannula;
two 30-gauge cannulas;
two medicine cups;
capsulorhexis forceps;
forceps;
a lens hook;
a paracentesis blade;
a keratome blade; and
a pack of sterile cotton tipped applicators.

15. The ultrasonic surgical handpiece according to claim 1 further including a surgical sheet secured about the connecting body and being designed so it can be draped over the housing.

16. The ultrasonic surgical handpiece according to claim 1 further comprising:
an angled slot in the blade; and
a pin engaging an angled surface of the slot;
wherein vibrations of the blade and engagement of the pin with the slot cause a side-to-side movement of the blade.

17. The ultrasonic surgical handpiece according to claim 16 further comprising a sheath surrounding the blade and the fluid lines in the vicinity of the blade, wherein the pin is mounted on the sheath and is stationary.

18. The ultrasonic surgical handpiece according to claim 16 further comprising a sheath surrounding the blade and the fluid lines in the vicinity of the blade and a second transducer located on the sheath, wherein the pin is mounted on the second transducer and is vibrated axially with respect to the blade while in contact with the angled surface of the slot.

19. The ultrasonic surgical handpiece according to claim 16 wherein the pin is mounted on the housing and is stationary.

20. The ultrasonic surgical handpiece according to claim 16 further including a second transducer located on the housing and wherein the pin is mounted on the second transducer and is vibrated axially with respect to the blade while in contact with the angled surface of the slot.

21. The ultrasonic surgical handpiece according to claim 1 further comprising:
a pin engaging a side of the blade; and a second transducer vibrating the pin perpendicularly to the axial movement of the blade, wherein engagement of the pin with the side of the blade causes a side-to-side movement of the blade.

22. The ultrasonic surgical handpiece according to claim 21 further comprising a sheath surrounding the blade and the fluid lines in the vicinity of the blade, wherein the pin is mounted on the second transducer and the second transducer is mounted on the sheath.

23. The ultrasonic surgical handpiece according to claim 21 wherein the pin is mounted on the second transducer and the second transducer is mounted on the housing.

24. The ultrasonic surgical handpiece according to claim 1 wherein the blade has a lateral curved edge and further comprising:

a pin engaging a side of the blade at the lateral curved edge; and wherein engagement of the pin with the curved edge of the blade causes a side-to-side movement of the blade.

25. The ultrasonic surgical handpiece according to claim 24 further comprising a sheath surrounding the blade and the fluid lines in the vicinity of the blade, wherein the pin is mounted stationary on the sheath.

26. The ultrasonic surgical handpiece according to claim 24 wherein the pin is mounted stationary on the housing.

27. The ultrasonic surgical handpiece according to claim 1 further comprising:

an electromagnetic coil;

a section of magnetic material on the blade adjacent the coil;

wherein electrical operation of the coil produces an alternating magnetic field that causes a side-to-side movement of the blade.

28. The ultrasonic surgical handpiece according to claim 27 further comprising a sheath surrounding the blade and the fluid lines in the vicinity of the blade, wherein the electromagnetic coil is mounted stationary on the sheath.

29. The ultrasonic surgical handpiece according to claim 27 wherein a pin is mounted stationary on the housing.

30. A disposable sterile surgical pack comprising the ultrasonic surgical handpiece according to claim 1 and at least one of a prep tray;
a pair of scissors;
an ear/ulcer syringe;
an eye speculum;
two to four syringes of various sizes;
a hydrodissection cannula;
two 30-gauge cannulas;
two medicine cups;
capsulorhexis forceps;
forceps;
a lens hook;
a paracentesis blade;
a keratome blade; and
a pack of sterile cotton tipped applicators.

* * * * *